US00PP22297P3

(12) United States Plant Patent
Werner et al.

(10) Patent No.: US PP22,297 P3
(45) Date of Patent: Dec. 6, 2011

(54) *CERCIS* PLANT NAMED 'MERLOT'

(50) Latin Name: ***Cercis canadensis and canadensis* var. *texensis***
Varietal Denomination: Merlot

(76) Inventors: Dennis James Werner, Raleigh, NC (US); Layne Karlton Snelling, Cary, NC (US)

( * ) Notice: Subject to any disclaimer, the term of this patent is extended or adjusted under 35 U.S.C. 154(b) by 0 days.

(21) Appl. No.: 12/653,814

(22) Filed: Dec. 21, 2009

(65) Prior Publication Data

US 2010/0205702 P1 Aug. 12, 2010

Related U.S. Application Data

(60) Provisional application No. 61/207,211, filed on Feb. 10, 2009.

(51) Int. Cl.
*A01H 5/00* (2006.01)

(52) U.S. Cl. ..... Plt./216

(58) Field of Classification Search ..... Plt./216
See application file for complete search history.

(56) References Cited

U.S. PATENT DOCUMENTS

PP19,654 P2 * 1/2009 Swanson et al. ..... Plt./216

* cited by examiner

*Primary Examiner* — June Hwu

(57) ABSTRACT

*Cercis* 'Merlot' is a new and distinct variety of redbud that has the following unique combination of desirable features that are outstanding in a new variety.

1. Moderate vigor resulting in moderate plant size.
2. Ease of asexual propagation using chip-budding.
3. Semi-upright growth habit.
4. Emerging foliage with deep purple color, transitioning to burgundy and eventually green during the growing season.
5. Glossy leaf surface.
6. Bright lavender flowers produced in abundance during the spring.
7. Low female fertility resulting in reduced pod set.

3 Drawing Sheets

Latin name of the genus and species: Genus: *Cercis*. Species: hybrid between *canadensis* and *canadensis* var. *texensis*.

Variety denomination: The inventive cultivar of *Cercis* disclosed herein has been given the variety denomination 'Merlot'.

This application claims the benefit of priority under 35 U.S.C. 119(e) of U.S. Provisional Application No. 61/207,211 filed on Feb. 10, 2009.

BACKGROUND OF THE INVENTION

The present invention relates to a new and distinct variety of *Cercis* (redbud) grown as an ornamental tree for home and commercial landscapes. Redbud is typically grown as a small tree for its attractive purple flowers that are borne in the spring, and sometimes for its interesting foliage color (purple, variegated, or golden leaf forms).

The new and distinct variety of redbud resulted from a formal breeding program established by the inventors in Raleigh, N.C., United States.

One of the objectives of the breeding program was to develop a purple leafed form of redbud that exhibited the foliage character and growth habit of the Texas redbud (small, glossy leaves and semi-upright growth habit). 'Merlot' originated as a second generation descendant from a cross of *Cercis canadensis* var. *texensis* 'Texas White' (sometimes referred to as 'Oklahoma White' in the trade)×'Forest Pansy' (*Cercis canadensis*) made in 1998. 'Texas White' was used as the female parent in the hybridization. 'Texas White' (unpatented) was released in the late 1960's, and is described as a white flowered form of *Cercis canadensis* var. *texensis*. 'Forest Pansy' (U.S. Plant Pat. No. 2,556) is a purple leaf form of eastern redbud (*Cercis canadensis*) discovered in 1947 in McMinville, Tenn. Both parents are commonly available in commerce.

The seeds resulting from the 1998 hybridization process were harvested in fall of 1998 and germinated in a greenhouse in Raleigh, N.C. in the winter of 1999. The resulting 113 seedlings were planted in a field planting in Jackson Springs, N.C., isolated from other redbuds, in spring 1999. Many of these plants flowered in summer 2002, and seed was collected off of all plants that produced seed. This seed was germinated in a greenhouse in Raleigh, N.C. in the winter of 2003. From these approximately 100 seedlings, 4 seedlings showing dark purple leaves were selected and grown in the greenhouse in 2003. These 4 seedlings were transplanted to the field in spring, 2004, and one plant, designated NC2004-6, was selected for its glossy purple leaf color, attractive lavender flower color, and semi-upright growth habit. This original plant demonstrated characteristics identical to those subsequently expressed on other plants when propagated by chip budding. This single plant is the subject of the present invention 'Merlot'.

The distinguishing traits of 'Merlot' are its distinctive leaves (thick, glossy, and purple color), attractive bright lavender flowers that are borne in abundance, and its semi-upright growth habit. The cultural requirements for 'Merlot' are well-drained soil, full sun, and moderate moisture. 'Merlot' exhibits no serious pest or disease problems known to the inventors.

The closest comparisons known to the inventors are the cultivars 'Forest Pansy' (U.S. Plant Pat. No. 2,556), the grandparent of 'Merlot', and 'Greswan' (U.S. Plant Pat. No. 19,654). Plants, leaves, and flowers of this new variety differ from both 'Forest Pansy' and 'Greswan'. In direct comparisons of the 3 cultivars in the inventor's experimental trials, plants of 'Merlot' are consistently more compact and more upright in growth habit compared to 'Forest Pansy' and 'Greswan'. Flowers of 'Merlot' are lavender as compared to the typical purple of 'Forest Pansy' and 'Greswan'. Compared to 'Forest Pansy' and 'Greswan', leaves of 'Merlot' are smaller, thicker, and have a distinct glossy appearance typical of its 'Texas White' grandparent. 'Merlot' differs from the 'Texas White' grandparent in having lavender flowers and purple leaves, compared to the white flowers and green leaves of 'Texas White'. 'Merlot' is clearly distinct from its original grandparents, and 'Greswan'.

The first asexual propagation of 'Merlot' was conducted by Alex and Harald Neubauer of Hidden Hollow Nursery on behalf of the inventors in fall 2006 in Belvidere, Tenn. 'Merlot' has subsequently been propagated in the same location in years 2007 and 2008. In all cases, the original plant selection was propagated asexually by chip budding in late summer onto *Cercis canadensis* rootstock. Such budded trees heal rapidly, and resume normal growth the following spring after budding. Five plants derived from chip budding of the variety were established in test plots in Jackson Springs, N.C. in February, 2008. During all asexual propagation, the characteristics of the original plant have been maintained. Plants derived from chip budding exhibit characteristics identical to those of the original plant, and no aberrant phenotypes have appeared.

Performance evaluation of the original plant and budded trees for 5 years and 2 years, respectively, in Jackson Springs, N.C. demonstrate this variety to be relatively consistent in its characteristics even under the different growing conditions associated with yearly climatic variation.

Plants of the new variety are only moderately vigorous after establishment in the field, being less vigorous and more compact than most cultivars of redbud. Young plants have averaged about 0.54 meters of growth per year. Plants are semi-upright in growth habit. Flowering typically occurs on previous season's growth in the second year after budding. The inflorescence is papillonaceous, and shows a bright lavender flower color. Flowering usually begins in late March to early April in Jackson Springs, N.C., and typically continues through mid to late April, depending on weather conditions. An individual flower persists for about 10 days, depending on temperature. Fertility of flowers is low, and the new cultivar sets very few fruit pods and seed. This is considered an asset in landscape settings.

'Merlot' is distinguished from other related known cultivars based on the unique combination of traits including moderate vigor, semi-upright growth habit, unique leaf character (small, glossy and purple), abundant production of bright lavender flowers, and low fruit production.

The new variety has been named the MERLOT cultivar. No public sale of 'Merlot' has yet taken place at the time of application. First public sale is anticipated to occur in January, 2010.

SUMMARY OF THE INVENTION

'Merlot' is a new and distinct variety of redbud that has the following unique combination of desirable features outstanding in a new variety. In combination these traits set 'Merlot' apart from all other existing varieties of redbud known to the inventors.

1. 'MERLOT' has moderate vigor resulting in smaller tree size than typical eastern redbud.
2. 'MERLOT' is asexually propagated using chip budding.
3. 'MERLOT' demonstrates semi-upright growth habit.
4. 'MERLOT' has attractive glossy-purple leaves in the spring, turning to burgundy and ultimately green as the growing season progresses. Leaves are smaller and thicker than typical eastern redbud.
5. 'MERLOT' exhibits low female fertility and reduced seed set, resulting in less opportunity for seedlings to originate in the landscape setting.
6. 'MERLOT' has bright lavender flower color.

BRIEF DESCRIPTION OF THE DRAWINGS

The photographs in the drawings were made using digital photography techniques, and show the colors as true as reasonably possible by digital photography. Colors in the photographs may differ slightly from the color values cited in the detailed botanical description, which accurately describe the colors of the new *Cercis* variety 'MERLOT'. All photographs were taken from the five-year-old plant growing at Jackson Springs, N.C.

DETAILED BOTANICAL DESCRIPTION OF THE VARIETY

Figure 1:
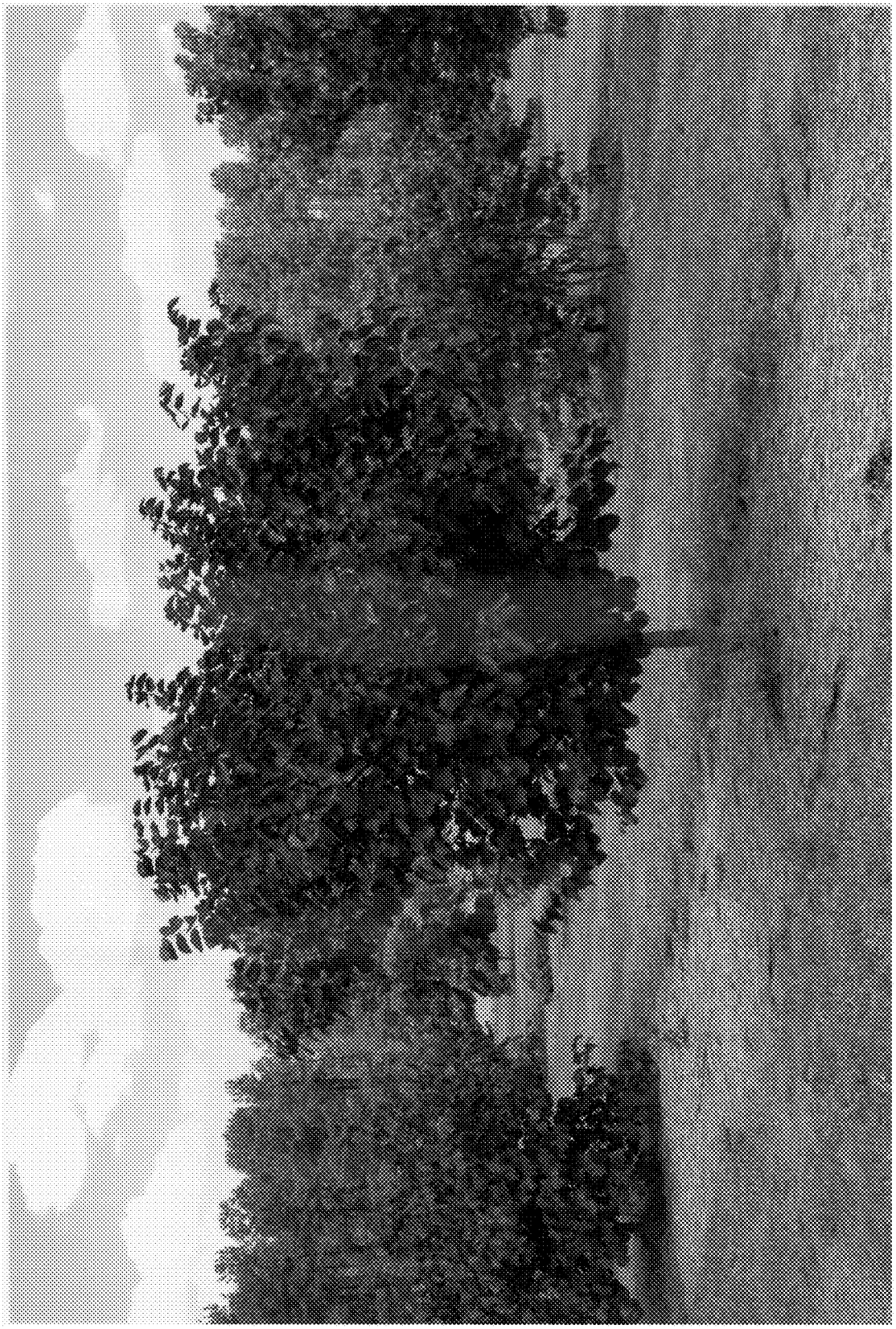
FIG. 1 shows a typical plant of 'MERLOT', showing the compact growth, upright habit, and purple leaves.
Figure 2:
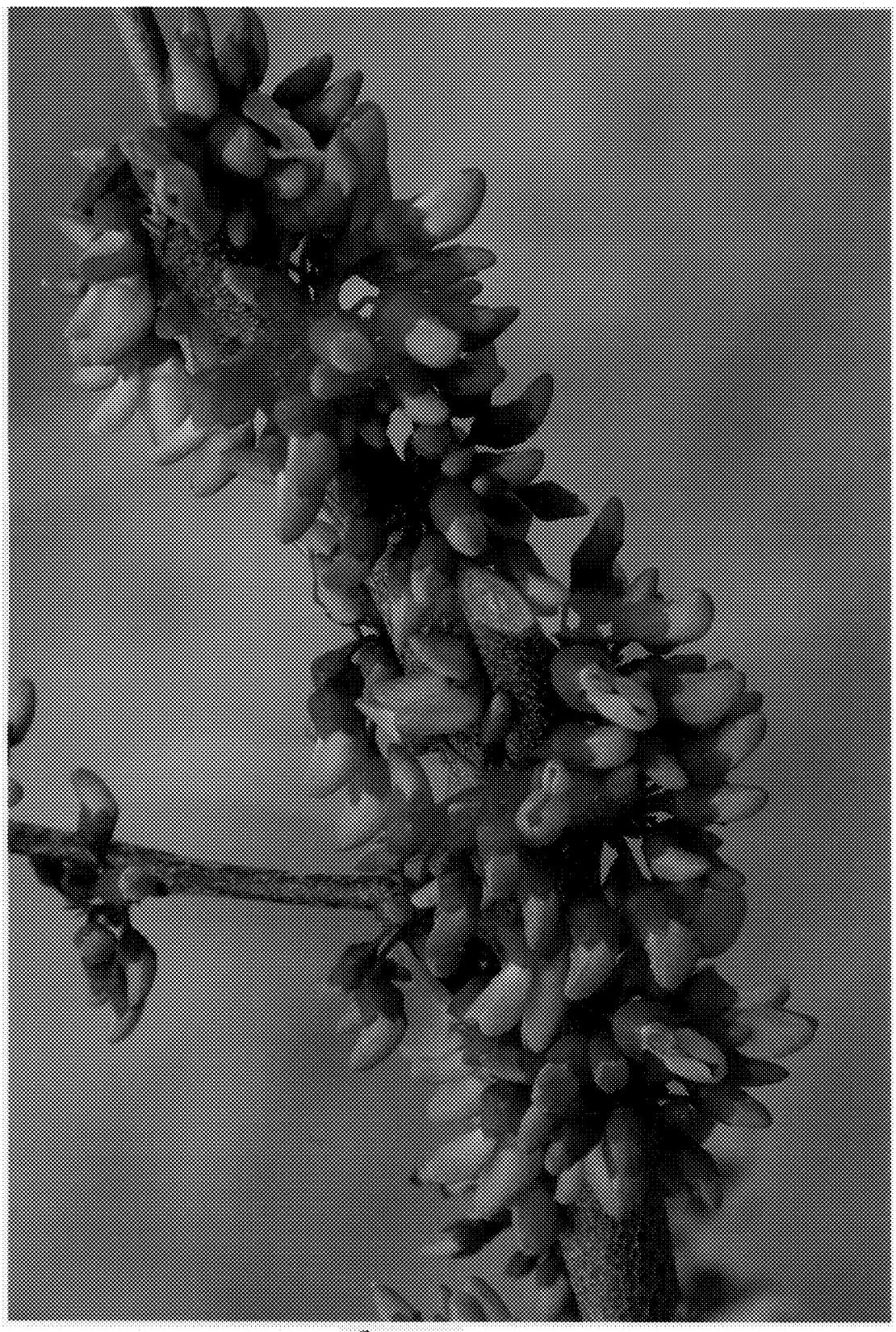
FIG. 2 shows a close-up view of the inflorescence of 'MERLOT', showing the lavender color of the individual flowers in the inflorescence.
Figure 3:
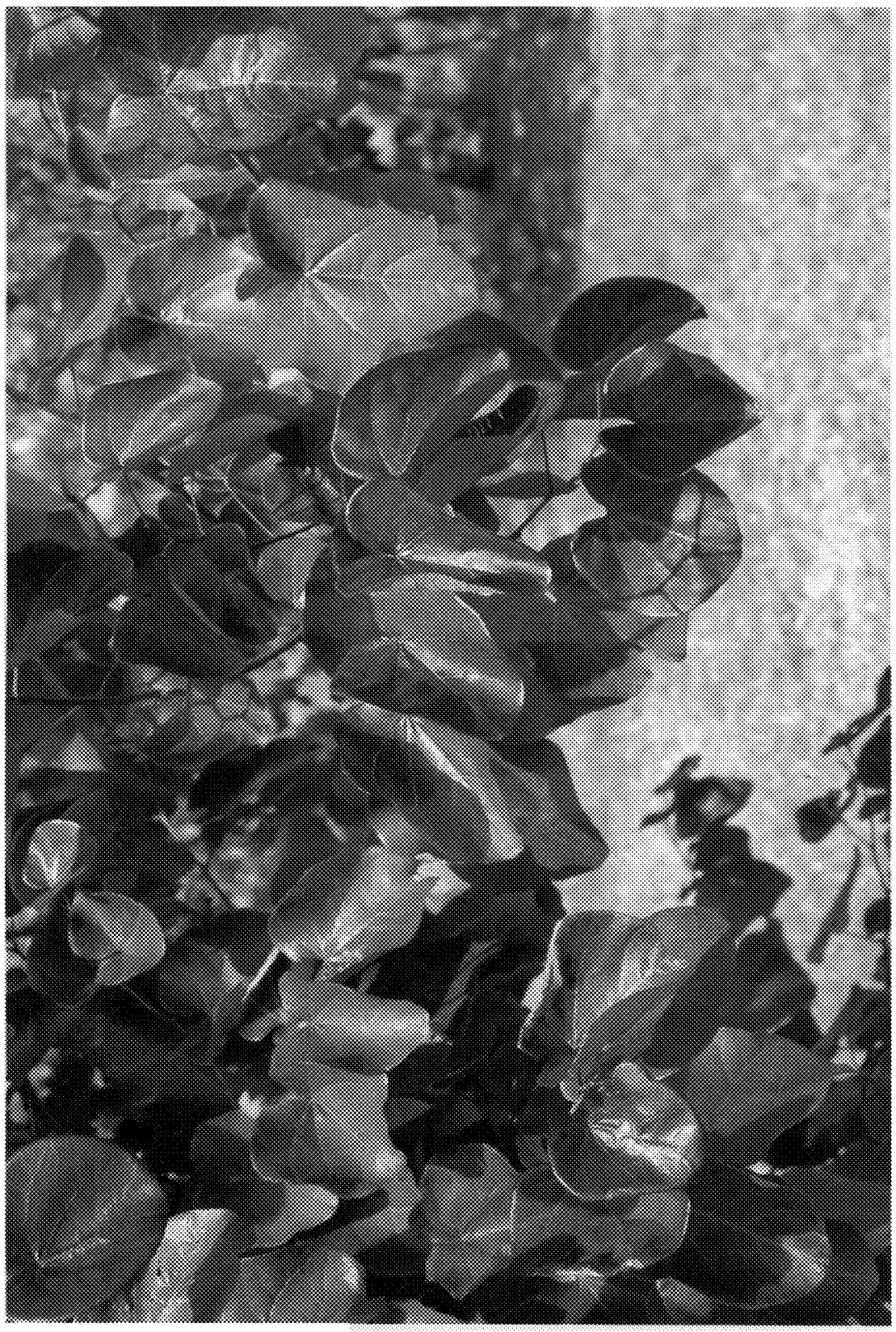
FIG. 3 shows the typical coloration and form of leaves of 'MERLOT'. This figure shows both recently formed and older leaves.

The following is a detailed description of the botanical and ornamental characteristics of the subject redbud 'MERLOT'. Color data are based on The Royal Horticultural Society Colour Chart, The Royal Horticultural Society, London, 2007 edition. Where dimensions, sizes, colors and other characteristics are given, it is to be understood that such characteristics are approximations of averages set forth as accurately as practicable.

The descriptions reported herein are from the original five-year-old tree growing at the research station in Jackson Springs, N.C.

Genus: *Cercis*

Species: Hybrid between *canadensis* and *canadensis* var. *texensis*

Denomination: 'MERLOT'

Commercial classification: Tree, deciduous

Common name: Redbud

Type: Ornamental

Uses: Small landscape tree for residential and commercial landscapes

Cultural requirements: Full sun exposure, well-drained soil, and moderate moisture.

Parentage: 'MERLOT' is a second-generation hybrid that resulted from the original cross pollination of *Cercis canadensis* var. *texensis* (Texas redbud) 'Texas White'× *Cercis canadensis* (eastern redbud) 'Forest Pansy'.

Plant description:

*Blooming period.*—Early to mid spring, late March to early April in central North Carolina.

*Blooming habit.*—Flower buds formed both on one-year-old wood, and on older wood.

*Vigor.*—Moderate vigor.

*Plant habit.*—Dense growth, semi-upright growth habit.

*Height and spread.*—2.7 meter height and 2.3 meter spread.

*Hardiness.*—To date, hardy to negative 12.8 degrees Centigrade. Not tested below this temperature. Anticipated adapted from USDA hardiness zones 6-9.

*Propagation.*—Chip-budding onto seedling rootstock, typically in late summer in the southeastern U.S.

*Root system.*—Fibrous.

*Seasonal interest.*—Bright lavender flowers in spring, and glossy purple leaves from spring through mid to late summer.

*Disease and pest susceptibility and resistance.*—No particular susceptibility or resistance.

*Special growing requirements.*—None. Best grown in full sun to partial shade in moderately well drained soil.

Trunk:

*Dimensions.*—0.3 m circumference measured 0.15 m above soil line.

*Bark surface.*—Slightly rugose.

*Color.*—Lighter sectors=blue-green (122D). Darker sectors=grayed-green (188A).

Stems:

*Shape.*—Stem cross section is circular.

*Length.*—Average 0.45 m per year of growth.

*Color.*—Yellow-green (144B) on recently formed shoots. Brown (N200A) on two-year-old stems.

*Diameter.*—5 mm near terminal portion of stem on mature one-year-old stems.

*Stem surface.*—Glaucous.

*Pubescence.*—Lacking.

*Internode length.*—1.9 cm between nodes.

*Lenticels.*—Numerous, tiny. Color (165C).

*Lenticel shape.*—Round.

Foliage:

*Type.*—Deciduous.

*Leaf arrangement.*—Alternate.

*Leaf division.*—Simple.

*Leaf shape.*—Obcordate to reniform. Occasionally broadly ovate.

*Leaf base.*—Cordate.

*Leaf apex.*—Obtuse.

*Leaf venation.*—Reticulate.

*Leaf surface (abaxial and adaxial).*—Glaucous.

*Leaf margin.*—Entire.

*Leaf attachment.*—Petiolate.

*Petiole dimensions.*—4.4 cm length. 2.0 mm width at base tapering to 1.0 mm at apex (nearest to leaf blade).

*Petiole shape.*—Round.

*Petiole color.*—Immature leaf (N92A). Mature leaf (N79A).

*Petiole surface.*—Smooth, lacking pubescence.

*Leaf color (immature leaf).*—Adaxial side=N77A. Abaxial side=59A.

*Leaf color (mature leaf).*—Adaxial side=N137A. Abaxial side=59A.

*Vein color (abaxial surface).*—Immature leaf (60A). Mature leaf (59C).

*Leaf length.*—10.1 cm from leaf tip to base of midvein/apex of petiole. 12.8 cm from leaf tip to base of leaf blade.

*Leaf width.*—13.1 cm.

*Foliar fragrance.*—None detectable.

*Stipules.*—None present.

*Causes for variation in color.*—Under normal sunlight, new foliage emerges deep purple (N77A) that grades to burgundy (N137A) to green (147A) over the growing season.

Flowers:

*Inflorescence.*—Papillonaceous flowers arranged in a small cluster.

*Number of flowers per cluster.*—3 to 7.

*Arrangement.*—Sessile clusters.

*Location.*—Nodes of previous years growth, and along older stems and occassionally the trunk (cauliflory).

*Length of bloom.*—2-3 weeks, depending on weather conditions.

*Flower length.*—1.0 cm from base of calyx to tip of keel.

*Flower width.*—3-4 mm immediately prior to anthesis.

*Flower depth.*—8 mm.

*Pedicel length.*—6 mm.

*Pedicel diameter.*—0.5 mm.

*Pedicel shape.*—Round.

*Pedicel color.*—Purple group (N77A).

*Pedicel surface.*—Smooth.

*Flowers persistent or self-cleaning.*—Self-cleansing.

*Flower fragrance.*—Lacking.

*Lastingness of the overall inflorescence.*—2-3 weeks.

*Lastingness of an individual flower.*—3-5 days.

Flower bud:

*Shape.*—Broadly oval.

*Color.*—Purple group (N77A).

*Surface.*—Smooth.

*Diameter.*—1.0 to 1.5 mm.

*Length.*—3 to 5 mm.

Petals:

*Number.*—5, lower 2 fused to form keel.

*Petals fused or unfused.*—3 unfused, 2 fused.

*Standard (banner) color.*—Purple (N78C).

*Keel petal color.*—Purple (N78C).

*Wing petal color.*—Purple (N78C).

*Petal surface (adaxial).*—Smooth.

*Petal surface (abaxial).*—Smooth.

*Petal margin.*—Entire.

Calyx:

*Shape.*—Vase-shaped.

*Length.*—5 mm.

*Diameter.*—5 mm.

*Color (outer surface).*—Purple (N79A).

*Color (inner surface).*—Purple (N79A).

*Surface (inner).*—Smooth.

*Surface (outer).*—Smooth.

Sepals:

*Number.*—1 — fused.

*Color (adaxial surface).*—N79A.

*Color (abaxial surface).*—N79A.

*Surface (adaxial surface).*—Smooth.

*Surface (abaxial surface).*—Smooth.

Reproductive organs:

*Pistil.*—Dimensions: 1.1 cm length. 1-2 mm width. Color: Red-purple (59B). Surface: Smooth.

*Stigma.*—Shape: Elliptical. Length: Less than 1 mm. Width: Less than 1 mm. Color: Red-purple (59B).

*Style.*—Length: Less than 1 mm. Width: Less than 1 mm. Color: Red-purple (60D).

*Stamens.*—Number: 10. Fused or unfused at base: 9 fused at base. 1 free. Length: 8 mm. Width: Less than 1 mm. Color (filament): Red-purple (59B).

*Anthers.*—Shape: Round to slightly oblong. Length: Less than 1 mm. Width: Less than 1 mm. Color: Red-purple (59B). Immediately prior to anthesis.

*Pollen.*—Color: Yellow group (9B). Amount: Abundant.

*Ovary.*—Position: Superior. Shape: Elongate. Length: 1 cm. Width: 1.0 mm. Color: Red-purple (59B).

*Fruit.*—Type: Dried pod. Rarely develop to maturation due to low female fertility. Typically present early in growing season but aborts mid-summer. Arrangement: Borne along stems in a pendant manner. Color: Purple (N77A) 2-4 weeks after bloom, prior to abortion. Seed: None produced to date, likely due to complex genetic background of 'Merlot'.

Herbarium voucher: A voucher of 'Merlot' will be deposited into the Herbarium of North Carolina State University (NCSU) in Raleigh, N.C., USA upon patenting.

What is claimed is:

1. A new and distinct variety of redbud tree (*Cercis*) having the characteristics substantially as described and illustrated herein.

* * * * *